United States Patent [19]

Magnolato et al.

[11] 4,444,798

[45] Apr. 24, 1984

[54] PROCESS FOR REMOVING STIMULATING COMPOUNDS FROM COCOA

[75] Inventors: Danièle Magnolato, Blonay; Alain Isely, Montherod, both of Switzerland

[73] Assignee: Societe d'Assistance Technique pour Produits Nestle S.A., Lausanne, Switzerland

[21] Appl. No.: 397,978

[22] Filed: Jul. 14, 1982

[30] Foreign Application Priority Data

Jul. 22, 1981 [CH] Switzerland ................ 4778/81

[51] Int. Cl.$^3$ .............................................. A23G 1/00
[52] U.S. Cl. ................................. 426/422; 426/593; 426/427; 426/631; 426/431
[58] Field of Search ............... 426/593, 631, 422, 427, 426/431; 544/274, 275

[56] References Cited

U.S. PATENT DOCUMENTS 4,160,042 7/1979 Farr et al. .................. 426/422 X
4,282,264 8/1981 Magnolato .................. 426/422 X

FOREIGN PATENT DOCUMENTS 2342177 7/1974 Fed. Rep. of Germany .

OTHER PUBLICATIONS

Moncrieff, The Chemical Senses, 1944, Leonard Hill Ltd.: London, pp. 109-110.

Primary Examiner—Joseph M. Golian
Attorney, Agent, or Firm—Vogt & O'Donnell

[57] ABSTRACT

In a process for depurinizing cocoa, green or roasted cocoa beans are extracted with water at a temperature of from 40° to 60° C., the extract is treated with an adsorbent based on desugared and activated carob particles in order to remove the purines therefrom, and the beans are dried and roasted. The dried beans are preferably rehydrated using the depurinized extract after being concentrated and before final roasting.

The treated cocoa is useful for the production of beverages containing cocoa and, when the variant with reincorporation of the non-purine solids is applied, for the production of chocolate.

6 Claims, No Drawings

PROCESS FOR REMOVING STIMULATING COMPOUNDS FROM COCOA

This invention relates to a process for the treatment of cocoa to remove therefrom the stimulating purines theobromine and caffeine.

It is known that cocoa beans contain from 1 to 2% by weight of theobromine and about ten times less of caffeine. It has been a long-standing wish to prepare depurinised cocoa so that it may be used in the production of beverages or chocolate. Thus, U.S. Pat. Nos. 1,855,026; 1,073,441 and 1,925,326 propose the extraction of purines by chlorinated solvents, while U.S. Pat. No. 2,118,129 describes a method of recovering theobromine by forming an aqueous solution and separating cocoa solids by the formation of a salt which is obtained by adding an alkaline oxide. Both treatments involve chemical methods which are considered undesirable.

Finally, German Patent Application No. 2,342,177 describes the extraction of theobromine with hot water, but, on the one hand, the extracted theobromine is not recovered and, on the other hand, the cocoa mass which is obtained after separating the aqueous solution is unsuitable for the production of a high quality chocolate or a cocoa-containing beverage.

Applicants have found a process for the complete depurinisation of cocoa by purely physical means, with quantitative recovery of theobromine and caffeine and the use of depurinised cocoa in the production of cocoa-containing beverages and chocolate.

The process according to the present invention is characterised by the following stages:

(a) green or roasted cocoa beans are extracted with water at a temperature of from 40° to 60° C., (b) the aqueous extract is treated with an adsorbent, in subdivided form based on desugared and activated carob particles in order to adsorb theobromine and caffeine, (c) the beans are dried and roasted, and (d) theobromine and caffeine are recovered and the adsorbent is regenerated by washing at a temperature of from 80° to 100° C.

In a preferred variant, the beans which have been dried in stage (c) are rehydrated using the depurinised aqueous extract, preferably after concentration, in order to reincorporate the solids other than theobromine and caffeine which have been extracted. This reincorporation of the extracted solids makes it possible to obtain a more balanced cocoa, from the organoleptic point of view, which in particular is suitable for the production of chocolate.

The cocoa beans which are used may be green or roasted and are preferably in a crushed and hulled form. Whole beans may also be used, but longer extraction times are then required. Green beans are preferably used, as this allows a roasting operation to be avoided.

The adsorbent is based on desugared and activated carob particles. It contains fibrous residues from carob pods which are ground coarsely, the sugars of which have been extracted with hot water, the particles being dried.

These particles are then treated with an acid, then optionally deodorized for example by steam stripping. Any suitable acid may be used, for example hydrochloric, sulphuric or phosphoric acid, dilute or concentrated. Treatment with dilute hydrochloric acid over a period of from 1 to 3 hours at ambient temperature is suitable.

For practical reasons, a material of relatively regular granulometry is preferably used. The material is then sieved, the retained particles advantageously having average dimensions of from 0.3 to 5 mm and preferably from 0.5 to 4 mm.

The different stages of the process according to the present invention will now be presented:

(A) Extraction: the green or roasted beans, cracked and dehulled, are extracted with hot water (T: 40°–60° C.) over a period of from 3 to 6 hours, in a slurry system and with agitation. The weight ratio of beans to water is from 1:30 to 1:50. The loss of dry matter during extraction is from 15 to 18%. In addition to theobromine and caffeine which respectively represent from 1.2 to 1.5% and from 0.2 to 0.5% of the dry weight of the beans, the aqueous extract contains mainly carbohydrates, mineral salts, organic acids and polyphenols. The extraction time varies inversely with the temperature.

(B) Adsorption: theobromine and caffeine may be adsorbed quantitatively and selectively on desugared and activated carob particles as indicated above. In order to achieve this, the aqueous extract of beans containing from 15 to 18% of dry matter of the cocoa used is brought into contact with the adsorbent, either in a column, or in a slurry tank with agitation. The weight ratio of adsorbent to extract is from 1:30 to 1:50. The treatment lasts from 2 to 4 hours at ambient temperature. The absence of theobromine and caffeine in the eluate is confirmed by high performance liquid chromatography (HPLC). The selectivity of the adsorption is determined from the dry matter of the eluate. The variation in amount of dry matter in the extract corresponds to the total of theobromine and caffeine contained in the beans (generally from 1.5 to 2.0%, depending on the type of beans considered).

(C) Drying and roasting: the beans which are extracted with hot water are dried in an oven with air circulation, at a temperature of from 60° to 80° C., over a period of from 2 to 4 hours. The beans are roasted according to a conventional process over a period of from 10 to 20 minutes at a temperature of from 115° to 125° C.

(D) Regeneration: the carob acting as adsorbent for the caffeine and theobromine is regenerated after the caffeine and theobromine have been quantitatively desorbed by washing with hot water at a temperature of from 80° to 100° C. for 1 hour in the form of a slurry, the weight ratio of adsorbent to water being from 1:30 to 1:100, effected in 2 or 3 successive treatments. The carob thus regenerated may be reused. However, it is found that there is a loss of about 5% in the adsorption capacity after each cycle. This loss may be compensated by adding a small quantity of fresh carob.

The variant which has been described above does not include the reincorporation of the non-purine solids which are extracted in stage (A). The beans, containing neither theobromine nor caffeine, are suitable for the production of cocoa powder used in the preparation of cocoa-containing beverages with or without malted cereals. This powder may also be solubilized by alkali treatment in conventional manner to obtain soluble powder. This alkali-treated cocoa is not suitable for the production of a chocolate, because of its mild character and reduced cocoa flavour intensity.

According to a preferred variant, the aqueous extract which is depurinised in stage (B) is concentrated, and is then used to rehydrate the beans dried in stage (C) before they are roasted, as described in stages (E), (F) and (G) below:

(E) Concentration: the aqueous extract freed from the theobromine and caffeine which it contained is concentrated under a vacuum of from 700 to 740 mm Hg and at a temperature of from 40° to 60° C. This is continued until a volume is produced which is from 1/40 to 1/20 of the starting volume.

(F) Rehydration (or reincorporation of solids other than theobromine and caffeine extracted in (B). The beans dried in (C) are brought into contact with the concentrate obtained in (E) over a period of from 8 to 12 hours at a temperature ranging from 20° to 30° C. The rehydration allows the reincorporation of from 13 to 16% of the solids.

(G) Drying (partial): the rehydrated beans with the extracted solids (excluding theobromine and caffeine) are dried over a period of from 1 to 2 hours at a temperature of from 70° to 80° C. in a oven with air circulation. Complete drying is undesirable, for it may give rise to the development of a "burnt" taste during roasting.

Experience has shown during tastings that the reincorporation of the extracted solids (stage (F)) is preferred in order to retain the organoleptic characteristics of the cocoa, in particular for the "cocoay" and "aroma" notes.

A chocolate which prepared from cocoa beans treated according to the above-described preferred variant of the process was submitted to a tasting panel.

In spite of a slight reduction in the cocoa-flavoured character, a very small reduction in the acid and bitter characteristics, a constancy in the mild and astringent characteristics and a very slight foreign taste, the chocolate was considered to be completely satisfactory.

The following Examples illustrate the operation of the process according to the present invention. The percentages and ratios in the Examples are based on the weight.

EXAMPLE 1

100 g of roasted, cracked and hulled BAHIA type beans containing 1.3% of theobromine and 0.2% of caffeine are extracted as a slurry with 4000 ml of water at 50° C. over a period of 4 hours. The loss of dry matter during extraction is 16%. The beans are recovered by screening, and dried for 4 hours at 70° C. The extract containing theobromine, caffeine and other extracted solids is passed through a column containing 100 g of desugared and activated carob particles at a flow rate of 15 ml/min. The theobromine and caffeine are adsorbed quantitatively on the carob. The eluate containing 14.5 g of dry matter consists mainly of carbohydrates, mineral salts, organic acids and polyphenols. It is concentrated under a vacuum of 720 mm Hg and at a temperature of 50° C. to a volume of 100 ml. This concentrate is brought into contact with the beans over a period of 12 hours at 25° C. in order to reintroduce the extracted solids. The beans, containing no theobromine or caffeine, are then dried over a period of 2 hours at 70° C. in a oven with air circulation and are final roasted at 120° C. for 15 min.

EXAMPLE 2

250 g of cracked and dehulled green beans of the GHANA type, containing 1.5% of theobromine and 0.15% of caffeine, are extracted as a slurry with 5000 ml of water at 100° C. over a period of 2 hours. The treated beans are separated by screening and washed with cold water to remove surface traces of theobromine and caffeine. The beans are then dried for 2 hours at 70° C. in a oven without air circulation, and roasted for 15 min at 120° C. The treated beans, containing neither theobromine nor caffeine and having lost 15% of their dry matter are tasted in the form of "Ganaches" (a mixture of cocoa, icing sugar and water, a sort of coarse unconched chocolate). The resulting product is tasteless and has lost a great deal of its "cocoay" note.

This Example shows that on the one hand, extraction at 100° C. is detrimental to the taste of the final product, and on the other hand, the absence of extracted solids has a significant effect on the organoleptic quality.

EXAMPLE 3

250 g of green beans of the GHANA type are extracted under the same conditions as in Example 2.

The extracted beans are washed with cold water before being dried for 4 hours at 70° C. in a oven with air circulation. The aqueous extract of the beans is slurried in a ratio of adsorbent to extract of 1:6, brought into contact with carob and maintained for 1 hour at ambient temperature.

Under these conditions, the 3.75 g of theobromine and the 0.38 g of caffeine extracted from the beans are adsorbed quantitatively and selectively on the 850 g of adsorbent. The aqueous extract is separated from the carob by filtration and concentrated by evaporation under vacuum to a volume of 250 ml. This concentrate is reincorporated in the treated beans, which were dried over a period of 10 hours at ambient temperature. As in the previous Example, the beans are then dried for 2 hours at 70° C. before being roasted for 15 min at 120° C.

The treated cocoa, containing neither theobromine nor caffeine, but in which the extracted solids have been reincorporated is tasted in the form of "Ganaches". The tasting results are substantially identical to those of the previous Example. This shows that even by reincorporating the extracted solids, the taste of the treated product is unsatisfactory, confirming the importance of the extraction temperature for the taste of the treated product. It is impossible to obtain an acceptable cocoa, free from theobromine and caffeine, when it has been extracted at 100° C. As shown by Example 1, an extraction which is longer, but is at a lower temperature (approaching 50° C.) is indispensible for the preparation of a product which is acceptable from the organoleptic point of view and which may be used in the production of chocolate.

EXAMPLE 4

10 g of green cocoa beans of the GHANA type containing 1.33% of theobromine are extracted with 200 ml of water at 60° C. over a period of 4 hours. The aqueous extract contains 133 mg of theobromine, that is, all of the theobromine which was initially present in the beans. This aqueous extract is brought into contact with 30 g of adsorbent. After 1 hour of reaction in a slurry with agitation at ambient temperature, 131 mg, i.e., 98.5% of the theobromine are adsorbed.

The aqueous extract (200 ml) is separated from the carob by filtration and is then concentrated by evaporation under vacuum to a volume of 20 ml. The beans are dried for 3 hours at 70° C. with air circulation and then brought into contact with the extract over a period of 12 hours at ambient temperature. The treated cocoa, containing neither theobromine nor caffeine, but in which the extracted solids have been reincorporated, is then partly dried over a period of 2 hours at 70° C. before being roasted for 20 min at 120° C.

The cocoa thus treated is tasted in the form of "Ganaches". The tasting shows that the product is completely acceptable, although slightly inferior to the one obtained from roasted beans of the BAHIA type (Example 1) (less "cocoay").

The 30 g of adsorbent containing 131 mg of theobromine are brought into contact with 1500 ml of water at 90° C. After 1 hour's stirring, 77 mg, i.e. 59% of the theobromine are desorbed. The carob is separated from the extract by filtration and brought into contact again with a fresh charge of 1500 ml of water at 90° C. The amount of theobromine desorbed after 1 hour's stirring is 51 mg, that is an additional 39%. 3 mg of theobromine then remain adsorbed on the carob, that is 2% of the starting theobromine which may be desorbed by washing with 1500 ml of water at ambient temperature.

The adsorbent thus regenerated is brought into contact with 200 ml of fresh bean extract containing 133 mg of theobromine. After a reaction time of 1 hour under the same conditions, 111 mg of theobromine are adsorbed, corresponding to a loss of fixation capacity of 15%. During the third cycle, the carob fixes 105 mg of theobromine, which corresponds to a capacity loss of 5%. This loss of 5% stabilizes during subsequent cycles. In order to maintain the initial adsorption capacity 15%, and subsequently 5% of the initial weight of carob, should be added in the form of fresh carob after each cycle.

We claim:

1. A process for treating cocoa to remove theobromine and caffeine therefrom comprising:
   (a) extracting green or roasted cocoa beans with water at a temperature of from 40° to 60° C. to form an aqueous extract containing theobromine, caffeine and other water soluble bean constituents;
   (b) treating the aqueous extract with an adsorbent of desugared and activated carob particles to adsorb theobromine and caffeine;
   (c) separating the adsorbent from the treated extract;
   (d) concentrating the treated extract;
   (e) drying the extracted beans;
   (f) rehydrating the dried beans with the concentrated extract to reincorporate the other water soluble bean constituents into the beans; and then
   (g) drying and roasting the rehydrated beans.

2. A process according to claim 1, wherein the aqueous extract in step (b) contains from 15 to 18% by weight of dry matter of the cocoa used and is contacted with the adsorbent in a column or in the form of a slurry at ambient temperature over a period of 2 to 4 hours in a weight ratio of adsorbent extract of from 1:30 to 1:50.

3. A process according to claim 1, wherein the treated aqueous extract is concentrated under a vacuum from 700 to 740 mm of mercury and at a temperature of from 40° to 60° C. to obtain a volume representing from 1/40 to 1/20 of the starting volume.

4. A process according to claim 3, wherein the beans are rehydrated by contact with the concentrated and treated extract over a period of 8 to 12 hours at a temperature of from 20° to 30° C.

5. A process according to claim 4, wherein the rehydrated beans are partly dried over a period of from 1 to 2 hours at a temperature of from 70° to 80° C.

6. The process of claim 1, wherein the adsorbent laden with theobromine and caffeine is regenerated by washing at a temperature of from 80° to 100° C.

* * * * *